United States Patent [19]
Loos

[11] Patent Number: 6,091,994
[45] Date of Patent: *Jul. 18, 2000

[54] PULSATIVE MANIPULATION OF NERVOUS SYSTEMS

[76] Inventor: Hendricus G. Loos, 3019 Cresta Way, Laguna Beach, Calif. 92651

[ * ] Notice: This patent is subject to a terminal disclaimer.

[21] Appl. No.: 09/144,762

[22] Filed: Aug. 31, 1998

Related U.S. Application Data

[63] Continuation-in-part of application No. 08/580,346, Dec. 28, 1995, Pat. No. 5,800,481.

[51] Int. Cl.⁷ ........................................................ A61F 2/00
[52] U.S. Cl. ............................................................. 607/100
[58] Field of Search ........................ 607/96–98, 100–102, 607/115, 148, 152; 600/552–558

[56] References Cited

U.S. PATENT DOCUMENTS

| | | | |
|---|---|---|---|
| 4,676,246 | 6/1987 | Korenaga | 128/399 |
| 4,763,666 | 8/1988 | Strian et al. | 600/557 |
| 4,860,748 | 8/1989 | Chiurco et al. | 607/96 |
| 5,315,994 | 5/1994 | Guibert et al. | 607/101 |
| 5,327,886 | 7/1994 | Chiu | 607/96 |
| 5,447,530 | 9/1995 | Guibert et al. | 607/107 |
| 5,800,481 | 9/1998 | Loos | 607/100 |

FOREIGN PATENT DOCUMENTS

| | | | |
|---|---|---|---|
| 9409850 | 5/1994 | United Kingdom | 607/88 |

*Primary Examiner*—Cary O'Connor
*Assistant Examiner*—Ryan Carter

[57] ABSTRACT

Method and apparatus for manipulating the nervous system by imparting subliminal pulsative cooling to the subject's skin at a frequency that is suitable for the excitation of a sensory resonance. At present, two major sensory resonances are known, with frequencies near ½ Hz and 2.4 Hz. The ½ Hz sensory resonance causes relaxation, sleepiness, ptosis of the eyelids, a tonic smile, a "knot" in the stomach, or sexual excitement, depending on the precise frequency used. The 2.4 Hz resonance causes the slowing of certain cortical activities, and is characterized by a large increase of the time needed to silently count backward from 100 to 60, with the eyes closed. The invention can be used by the general public for inducing relaxation, sleep, or sexual excitement, and clinically for the control and perhaps a treatment of tremors, seizures, and autonomic system disorders such as panic attacks. Embodiments shown are a pulsed fan to impart subliminal cooling pulses to the subject's skin, and a silent device which induces periodically varying flow past the subject's skin, the flow being induced by pulsative rising warm air plumes that are caused by a thin resistive wire which is periodically heated by electric current pulses.

12 Claims, 5 Drawing Sheets

40 MIN. 100-60 COUNT  <50 SEC ○
                       ≥50 SEC ●

_US 6,091,994_

PULSATIVE MANIPULATION OF NERVOUS SYSTEMS

Continuation-in-part of application No. 580,346, Dec. 28, 1995, now U.S. Pat. No. 5,800,481, Sep. 1, 1998.

BACKGROUND OF THE INVENTION

The invention relates to influencing the nervous system of a subject by pulsative stimulation of sensory receptors, relying on the mechanisms of sensory resonance and frequency modulation of spontaneous spike patterns, as discussed in U.S. Pat. No. 5,782,874. [1]. In that patent, the stimulation is provided by an external electric field applied to the skin of the subject. The electric field appears to cause a modulation of the spiking patterns of certain cutaneous receptors, so that a pulsative field gives rise to a frequency modulation (fm) of the produced spike trains. Afferent nerves carry the frequency modulated spike trains to the brain, where in certain neural circuits the evoked fm signals cause excitation of a resonance with observable physiological consequences. One such "sensory resonance" that occurs near ½ Hz causes sleepiness, relaxation, a tonic smile, ptosis of the eyelids, a tense feeling in the stomach, or sexual excitement, depending on the precise pulse frequency used. The ½ Hz sensory resonance can also be excited by magnetic fields, as discussed in U.S. Pat. No. 5,935,054 [2].

Another known sensory resonance occurs near 2.4 Hz and causes a slowing of certain cortical activities.

SUMMARY

Experiments have shown that sensory resonances can be excited by imparting cooling pulses to the skin, when the pulse frequency is set to the resonance frequency of the sensory resonance, and the pulses have a proper subliminal amplitude. The sensory resonance near ½ Hz causes autonomic responses characterized by relaxation, sleepiness, ptosis of the eyelids, a tonic smile, a "knot" in the stomach, or sexual excitement, depending on the precise frequency used. The sensory resonance near 2.4 Hz causes slowing of certain cortical activities and is indicated by a large increase in the time needed to count silently backward from 100 to 60, with the eyes closed. The described effects occur only if the amplitude of the cooling pulses falls in a certain range called the effective intensity window.

The stimulation is thought to involve the following. The subliminal pulsative cooling of the skin causes a slight frequency modulation (fm) of the spike trains that are produced by cutaneous thermoreceptors. The spiking is transmitted to the brain by afferent nerves that report skin temperature. The frequency modulation of the spike train from a single thermoreceptor cannot be spotted by the brain, because the fm variations in the spike train are swamped by the much larger stochastic spiking variations. However, if afferents of a large number of affected thermoreceptors synapse on a single summing neuron, then the fm variations add coherently in the hillock potential, whereas the stochastic variations largely even out. Consequently, the signal to noise ratio for the fm signal is increased, and the more so the larger the skin area exposed to the cooling pulses. The fm signal is demodulated by further neural circuitry and the resulting signal can cause excitation of a resonance in certain subsequent processing circuits. The upper bound of the effective intensity window is thought to arise from the action of nuisance guarding neural circuits that block substantial repeditive nuisance signals from higher processing. The lower boundary of the window is simply due to a detection threshold.

Reliance on periodic frequency modulation of afferent spike trains, together with exploitation of the resonance phenomenon, leads to a method and apparatus for manipulation of nervous systems by imparting subliminal cooling pulses to the subject's skin. The invention can be used by the general public to induce relaxation, sleep, or sexual excitement, and clinically for control and perhaps a treatment of tremors and seizures, as well as autonomic disorders, such as panic attacks.

The cooling pulses may be imparted to the skin by convective or conductive means. In the latter case heat is extracted from the skin in pulsative fashion by a fast Peltier junction that is placed on the skin. In the convective method, cooling is provided through convective and evaporative heat transfer by means of a pulsed air jet aimed at the skin of the subject, or alternatively by a device wherein a periodic air sink draws atmospheric air past the skin of a nearby subject, the periodic air sink being induced by pulsative rising warm air plumes produced by a thin resistive wire that is heated by current pulses passed by a field effect transistor which is controlled by voltage pulses from a generator.

Using the latter device, the 2.4 Hz sensory resonance has been explored, employing the silent count from 100 to 60 as a resonance detector. The measured counting times define an excitation footprint in the plane which has pulse power and pulse frequency as coordinates.

A compact embodiment is shown in the form of a battery powered device, in which the resistive wire and the voltage generator are contained in a single small casing.

DETAILED DESCRIPTION

In the excitation of sensory resonances by external electric [1] or magnetic [2] fields, the fields appear to induce in certain receptors a slight frequency modulation of their normal spontaneous stochastic spiking. Since cutaneous thermoreceptors exhibit spontaneous spiking and report skin temperature to the brain by frequency coding [3,4] or a more elaborate modulation [5], the question arises whether perhaps sensory resonances can also be excited through cutaneous thermoreceptors. It has been found in our laboratory that this is indeed the case; when temperature pulses of certain intensity and with a frequency near ½ Hz are induced in the skin, the subject experiences an autonomic nervous system response that involves sleepiness, relaxation, a tonic smile, ptosis of the eyelids, a "knot" in the stomach, or sexual excitement, depending on the precise frequency used. It has also been found that the 2.4 Hz cortical resonance can be excited thermally as well. For the physiological effects to occur, the temperature pulse amplitude must fall in a certain range, here called the effective intensity window. The intensities in the window are found to be deeply subliminal.

The discovery leads to a method and apparatus for manipulating nervous systems, wherein subliminal temperature pulses are induced in the skin by conductive, convective, or radiative means. The invention may be used by the general public as a sleeping aid or for facilitating relaxation or sexual arousal, and clinically for the control and perhaps a treatment of tremors and seizures as well as disorders of the autonomic nervous system, such as panic attacks.

Figure 3:
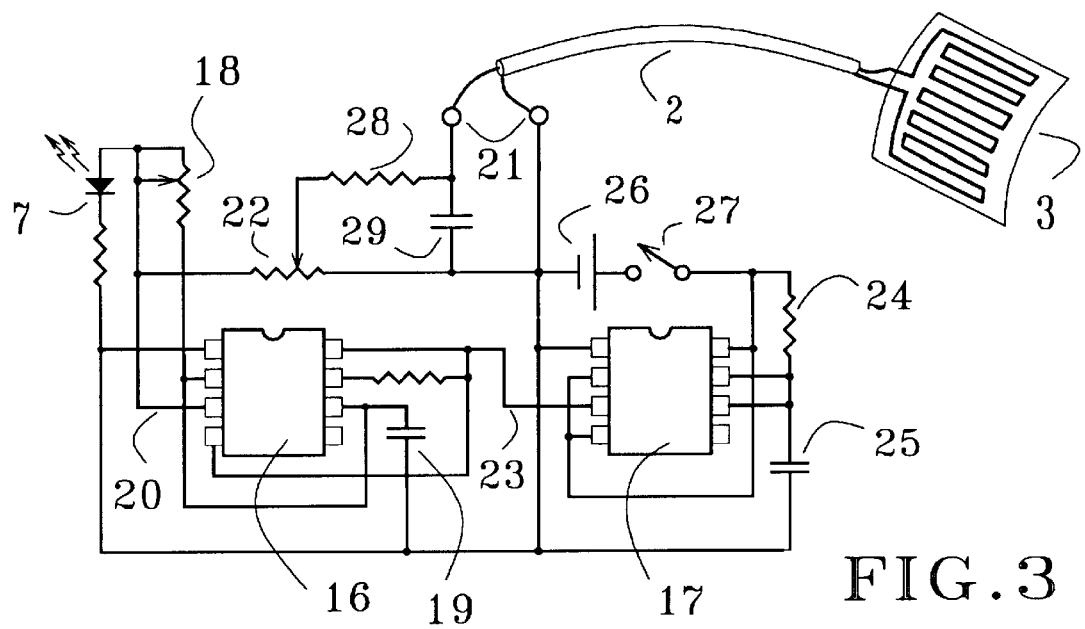
FIG. 3 shows a voltage generator connected to a heatpatch for delivering heat pulses to the skin of a subject.
Figure 4:
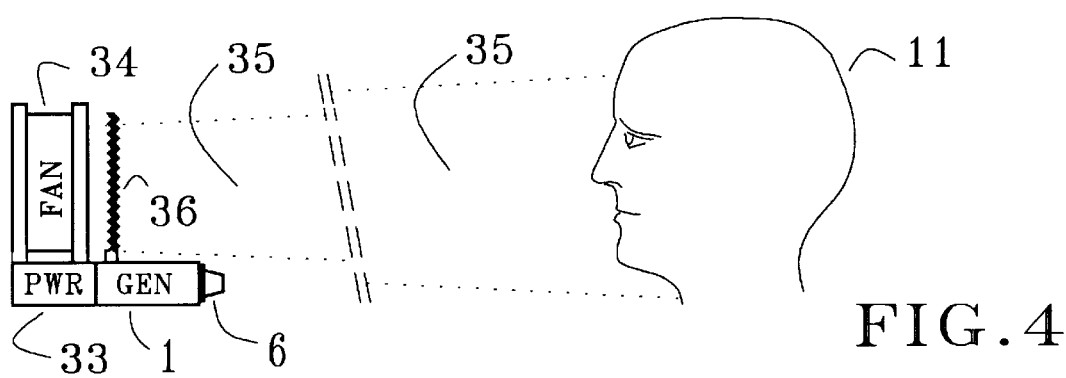
FIG. 4 depicts the delivery of heat pulses to the skin of a subject by an air jet with a periodic temperature.

An embodiment of the invention is shown in FIG. 3, where a resistive heat patch 3 is connected via a thin coaxial cable 2 to the output terminals 21 of a battery-powered voltage generator. The latter is built around two RC timers 16 and 17. Timer 16 (Intersil ICM7555) is hooked up for astable operation; it produces a square wave voltage with a frequency determined by potentiometer 18 and capacitor 19. The square wave voltage at output 20 drives the LED 7 and appears at one of the output terminals 21, after voltage division by potentiometer 22. The other output terminal is connected to the negative supply. Automatic shutoff of the voltage that powers the timer 16 at point 23 is provided by a second timer 17 (Intersil ICM7555), hooked up for monostable operation. Shutoff occurs after a time interval determined by resistor 24 and capacitor 25. Timer 17 is powered by a battery 26, controlled by a switch 27. Rounding of the square wave is provided by an RC circuit consisting of a resistor 28 and capacitor 29. The output terminals 21 are connected, via the cable 2, to the resistive heat patch 3, which therefore undergoes periodic changes of temperature when the generator is operating. When the heat patch 3 is placed on the skin, cutaneous thermoreceptors are exposed to a periodic temperature fluctuation, and the ½ Hz sensory resonance can be excited if the skin temperature oscillation has the proper amplitude. It turns out that for these amplitudes the skin temperature oscillation is subliminal. A battery voltage of 3 volt gives satisfactory results, but other battery voltages may be used or one may employ a power supply.

embodiment with convective heat pulse induction is depicted in FIG. 4. Shown are a power supply 33, labeled "PWR", that provides power for a fan 34, labeled "FAN"; the latter produces a jet 35 in the surrounding air. The jet is made to pass through a grid 36 resistor wires that are driven by voltage pulses from a generator 1, labeled "GEN", with pulse frequency tuning control 6. The voltage pulses cause the resistor wires to be heated in a periodic manner, with the result that the air jet temperature acquires a wave-like pattern that is convected downstream with the jet flow. Hence, a subject 11 whose face is exposed to the jet will undergo a pulsative heat flux to the skin. Experiments have shown that with this device the ½ Hz sensory resonance can be excited. In these experiments the flow of air over the subject's face was too slow to be sensed, and the periodic temperature fluctuations induced in the skin of the subject were subliminal as well. The apparatus is thus suitable for manipulating a subject's nervous system in a covert manner.

In the embodiments shown in FIGS. 3 and 4 periodic skin temperature variations are caused by heat pulses, but cooling pulses may be used instead. Depending on the ambient temperature, cutaneous warm receptors or cold receptors or both will respond to the cooling pulses by modulating their spike trains. The spike trains are transmitted to the brain by afferent nerves, so that the pulsative modulation brought on by the cooling pulses evokes a pulsative signal which can be used for manipulation of the nervous system, provided that the parameters of the cooling pulses are chosen appropriately. For instance, by tuning the pulses to the resonance frequency of a sensory resonance, the apparatus for imparting pulsative cooling to the skin can be used for exciting in the subject a sensory resonance.

Figure 2:
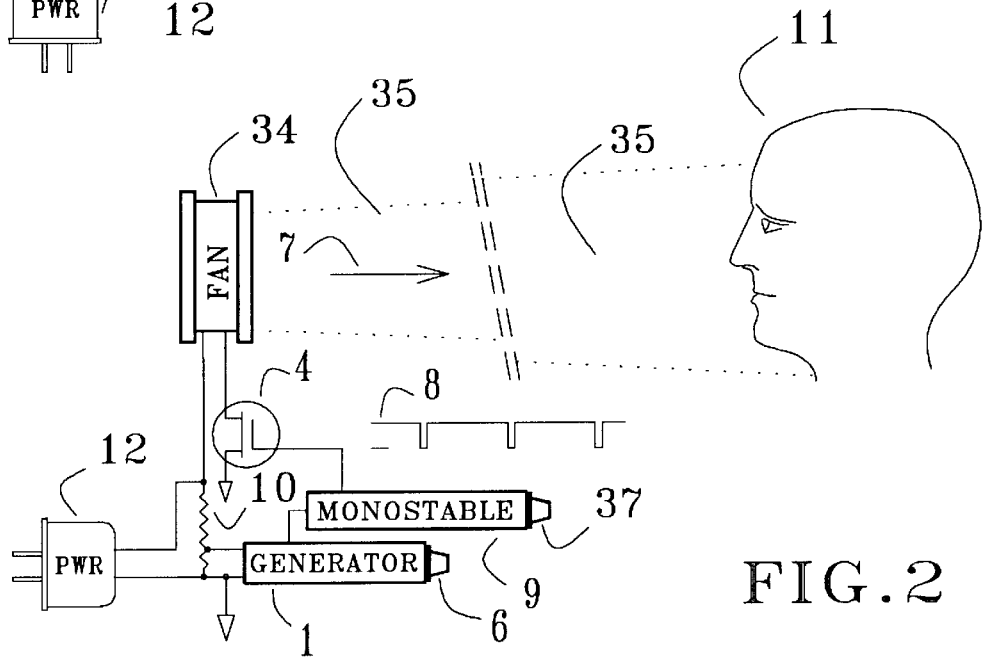
FIG. 2 shows an embodiment where pulsative cooling of the subject's skin is brought about by a fan powered by a voltage that is periodically interrupted.

In the convective mode, pulsative cooling may be imparted to the skin through a pulsing air jet produced by a fan that is powered by a pulsating voltage. An embodiment is shown in FIG. 2, where the fan 34 labeled "FAN" is powered via a field effect transistor 4 controlled by a signal 8 that is periodically interrupted. This signal is produced by the monostable multivibrator 9, labeled "MONOSTABLE", in response to a square wave voltage from the generator 1, labeled "GENERATOR". The width of the negative pulses in signal 8 is manually set by the pulse width control 37, and the frequency of the square wave output of the generator 1 is manually set with the tuning control 6. The supply voltage for the generator 6 is derived, through the resistive divider 10, from the output of the power supply 12, labeled "PWR", which is inserted into a wall power socket. The fan produces in the surrounding atmospheric an air jet 35 which has a momentum flux vector 7, defined as the integral, over a stationary plane that intersects the whole jet, of $vv_n \rho dA$, where v is the local air velocity vector, $v_n$ its component perpendicular to the surface element dA, and $\rho$ is the air density. The pulsative interruptions of the voltage to the fan cause the momentum flux vector of the jet to vary in pulsative manner, in this case by changing its magnitude. Hence heat will be extracted in pulsative manner from the skin of a subject 11 whose face is exposed to the jet, as the air velocity over the skin varies periodically. The pulse width control 37 is to be adjusted such as to make the amplitude of the cooling pulses fall inside the effective intensity window for the sensory resonance to be excited. An AC fan can be used, with the power to the fan modulated in a manner responsive to the voltage pulses from the generator. It is noted that the fan can induce pulsative air flow over the skin of a subject not positioned directly in the air jet. This is because the jet entrains ambient air in the manner discussed in ref. [9], and also because the fan takes in ambient air, thereby inducing an "intake" air flow in the surrounding atmosphere. Indeed, the device of FIG. 2 has been found effective for exciting the ½ Hz and 2.4 Hz sensory resonances, with the subject positioned several meters off the side of the jet.

Figure 1:
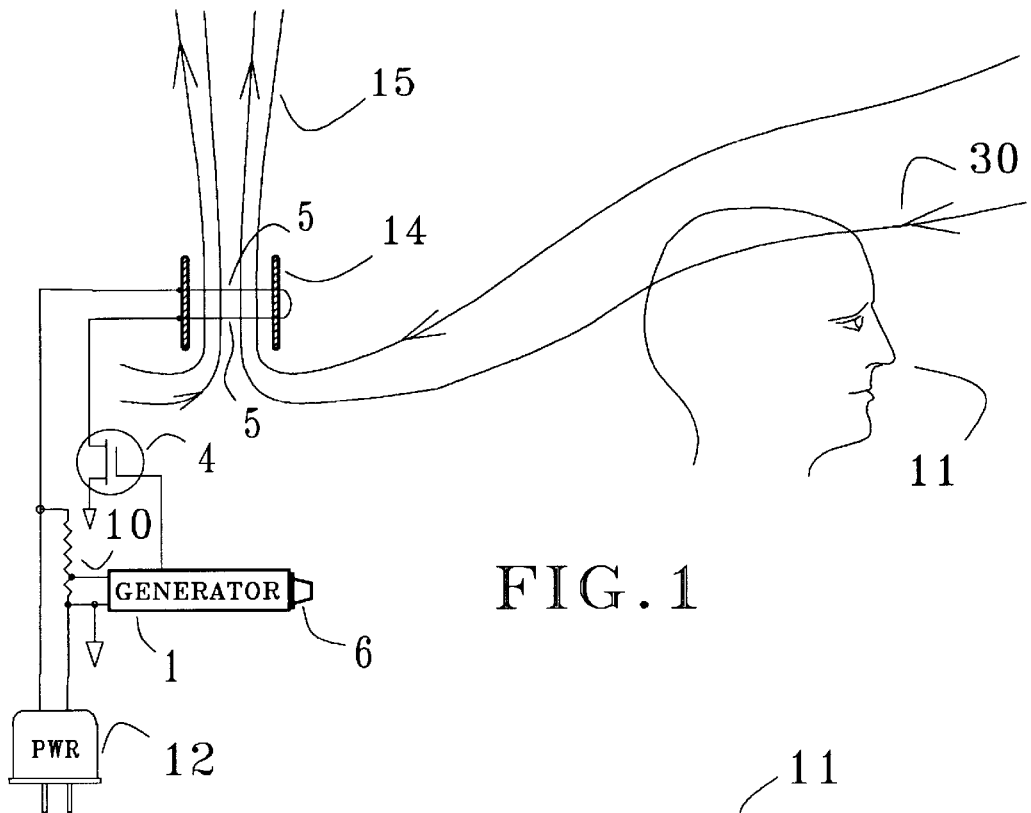
FIG. 1 shows a preferred embodiment where pulsative cooling of a subject's skin is achieved by a periodic air flow caused by a thermally induced air sink.

A preferred embodiment wherein pulsative cooling is imparted to a subject's skin in a silent manner is shown in FIG. 1, where the electric current through thin resistive wires 5, mounted in a hollow cylinder 14 such as to be in contact with ambient atmospheric air, is modulated by the field effect transistor 4, which is controlled by the square wave voltage from the generator 1, labeled "GENERATOR". The latter is powered by a relatively low supply voltage from a resistive divider 10, that receives supply voltage from a wall power supply 12, labeled "PWR". The frequency of the square wave from the generator 1 is set with the manual tuning control 6. The hollow cylinder 14 is mounted such that its axis is vertical. With this arrangement, the thin resistive wires 5 are heated periodically by the current pulses that are passed by the field effect transistor 4. As a result, the wire temperature varies in a pulsating manner, so that a warm air plume 15 develops periodically inside the cylinder 14, and rises by buoyancy. By virtue of its vertical motion, this plume draws air from the ambient atmosphere, thereby periodically creating an air sink in this region. This air sink draws atmospheric air from the surroundings, inducing an air flow 30 past the head of the nearby subject 11. The air flow is further enhanced by ambient air that is entrained by the rising warm air plume. Since the air sink is periodic, the air flow 30 varies in a periodic manner, and thus imparts pulsative cooling to the subject's skin. There may be only a single resistive wire 5, or several wires may be used in a parallel and serial combination such as to give an appropriate total resistance. AC power may be used to provide the current through the resistive wires 5, and the field effect transistor must then be replaced by an appropriate modulator. Optionally, the divider 10 can be omitted, so that the generator and the FET 4 have the same supply voltage.

In the embodiments shown in FIGS. 1 and 2, acoustic effects are induced in addition to the pulsative cooling of the subject's skin. In the arrangement of FIG. 2 the pulsative airflow of the jet past the face of the subject generally causes, by virtue of the ram effect, slight pulsations of the atmospheric pressure at the subject's ears. Moreover, the pulsating speed of the fan causes at its inlet a periodic air sink that acts as an acoustic source. Similarly, in the device of FIG. 1, the periodic air sink that occurs at the bottom of the cylinder 14 constitutes an acoustic monopole which radiates low frequency sound, and the periodic expansions of the air heated by the wire constitutes another sound source. Hence, in both cases sound with the generator frequency is induced at the subject's ears. Although this sound is inaudible because of its low frequency and intensity, it may cause excitation of sensory resonances through stimulation of the vestibular nerve, as discussed in U.S. Pat. No. 6,017,302[6]. Hence, the apparatus of FIG. 1 or FIG. 2 may excite sensory resonances simultaneously through two different sensory modalities, viz. cutaneous thermoreceptors and the vestibular end organ. One may expect considerable integration of these signals in the central nervous system, since the resonance frequencies for excitation by different sensory modalities are found to be nearly the same. However, the integration can be only partial, since habituation to the stimulation involved in sleeping aid applications of devices discussed here and elsewhere [1,2, 6,8] can be thwarted by changing to another sensory modality after a few nights. Therefore, when excitation of a sensory resonance occurs via skin temperature afferents as well as through the vestibular nerve, these exitations are expected to enforce each other only partially. The devices of FIGS. 1 and 2 are found to be effective as sleeping aids, but we have noticed a peculiar side effect in the form of a slightly unpleasant feeling that was not experienced with electric [1] or magnetic [2] field stimulation, or with the heat patch device of FIG. 3. The effect may perhaps be due to the involvement of multiple sensory modalities. The matter needs further investigation.

Figure 7:
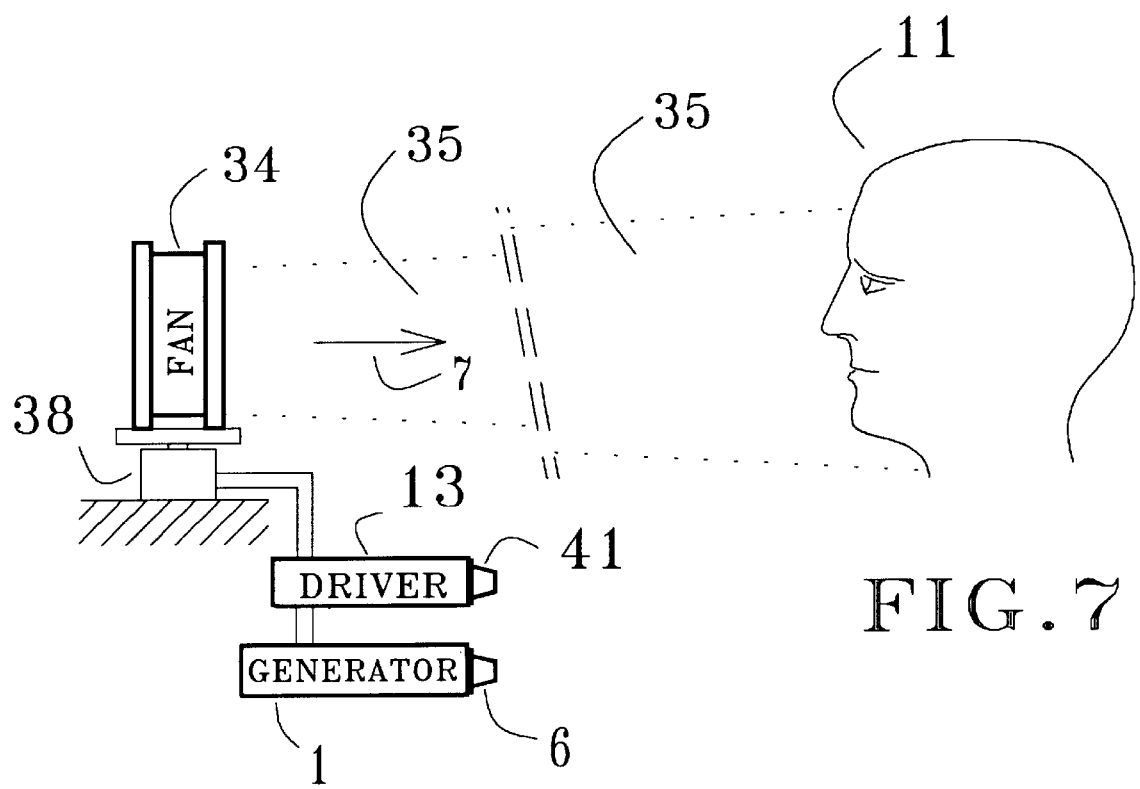
FIG. 7 shows an embodiment where pulsative cooling of a subject is obtained with a swiveling fan.
Figure 8:
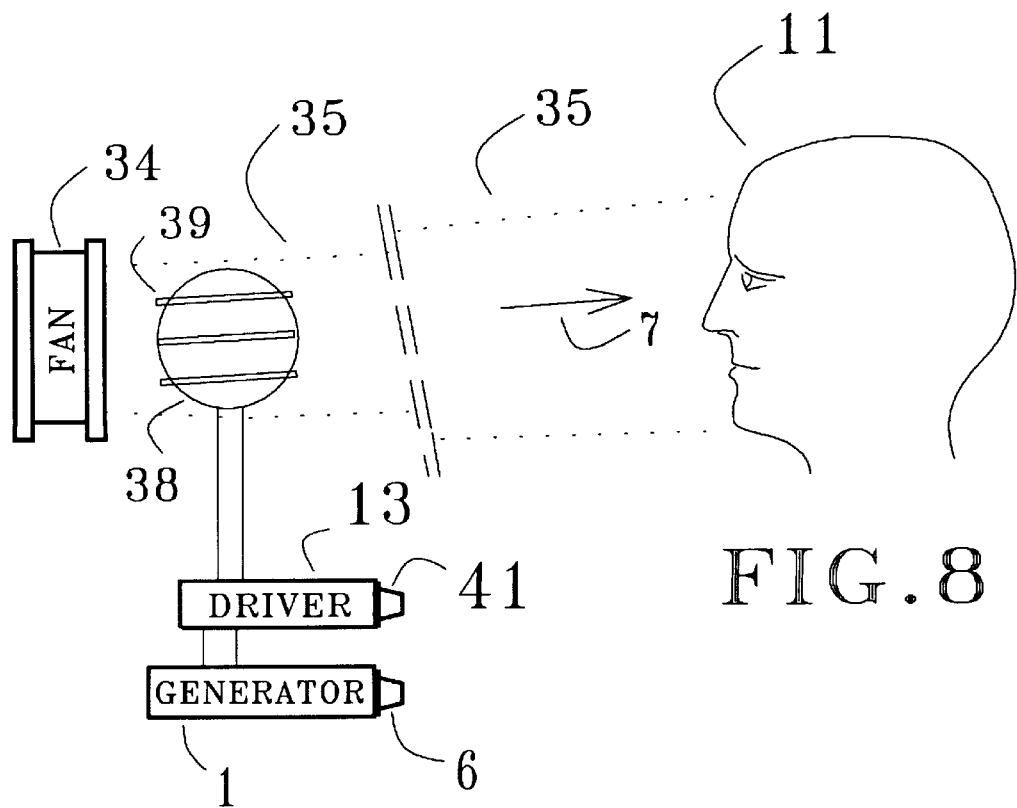
FIG. 8 shows an embodiment where pulsative cooling of a subject is obtained by an air jet that is periodicly deflected by vanes.

In the embodiment of FIG. 2 the pulsative variation of momentum flux vector 7 takes the form of a variation of the vector magnitude. Instead, one may vary the direction of the vector. Embodiments of this kind are shown in FIGS. 7 and 8. In FIG. 7, a DC or AC fan 34, labelled "FAN", is mounted on the shaft of a stepper motor 38 which is actuated by positive and negative pulses from the driver 13, labelled "DRIVER", which in turn receives a pulse signal from the generator 1, labelled "GENERATOR". In response to this signal, driver 13 produces a periodic signal, each period consisting of N positive pulses and N negative pulses, thereby causing the fan to swivel back and forth with an amplitude determined by the integer N selected with the amplitude control 41. The swivel motion of the fan causes the momentum vector 7 to change its direction in an oscillating manner, thereby imparting pulsative cooling to the skin of a properly positioned subject 11. The frequency of the pulsative cooling can be selected with the tuning control 6 of generator 1. The driver 13 can be structured in a number of well-known ways, for instance as a CMOS switch that causes switching between positive and negative pulses, together with a counter that controls the CMOS switch.

An alternate embodiment with a pulsative momentum vector direction is shown in FIG. 8, where the DC or AC fan 34, labelled "FAN", produces an air jet 35 that is made to pass through deflector vanes 39 mounted on the shaft of a stepper motor 38 that is controlled by the driver 13, labelled "DRIVER", which in turn receives pulses from the generator 1, labelled "GENERATOR". The stepper motor shaft rotates back and forth through a range that is set by the amplitude control 41 of driver 13. The latter outputs to the stepper motor a periodic signal, each period consisting of N positive pulses followed by N negative pulses. The pulses are derived from the output of generator 1; the latter has a frequency control 6. The oscillating vanes 39 provide a pulsative deflection to the air jet, and thereby a periodic direction variation to the momentum flux vector 7, which causes pulsative cooling to be imparted to the skin of a properly positioned subject 11. The driver 13 can have the same structure as driver 13 in FIG. 7, discussed above.

Figure 11:
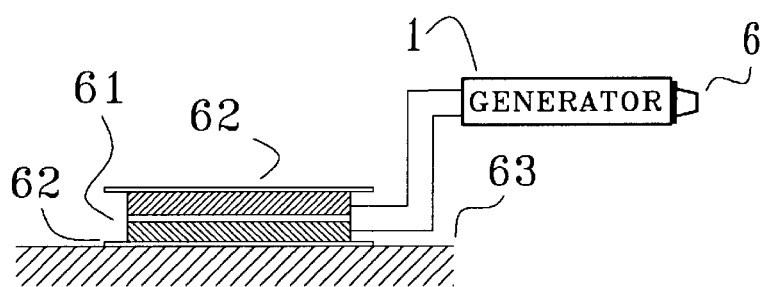
FIG. 11 shows a Peltier junction for imparting pulsative cooling of a subject's skin by conduction.

In the embodiments of FIGS. 7 and 8, cooling pulses are imparted to the skin by convective heat transfer, which is understood to include evaporative heat transfer as well. Alternatively, cooling pulses may be imparted to the skin by extracting heat through conduction, as in FIG. 11, where a fast Peltier junction 61 is placed in conductive contact on the skin 63 of the subject; the wording includes the case, shown in FIG. 11, that a thin electrically insulating sheet 62 is present between the junction and the skin. Such a sheet 62 may also be placed on top of the junction, as shown in FIG. 11. The Peltier junction 61 is driven by voltage pulses from the generator 1 labelled "GENERATOR", with tuning control 6.

The cooling pulses imparted to the skin may have pertinent parameters other than frequency and intensity. For instance, for the purpose of thwarting habituation to the stimulation, irregular features may be introduced in the generator pulses, such as short-term frequency variations of a chaotic or stochastic nature. A chaotic wave can also be used for upsetting pathological oscillatory modes in neutral circuits, thereby providing some measure of control of tremors, for instance in Parkinson patients.

Chaotic or stochastic heating or cooling pulses can cause excitation of a sensory resonance, provided that the pulses have a spectral peak of proper intensity close to the resonant frequency.

Figure 5:
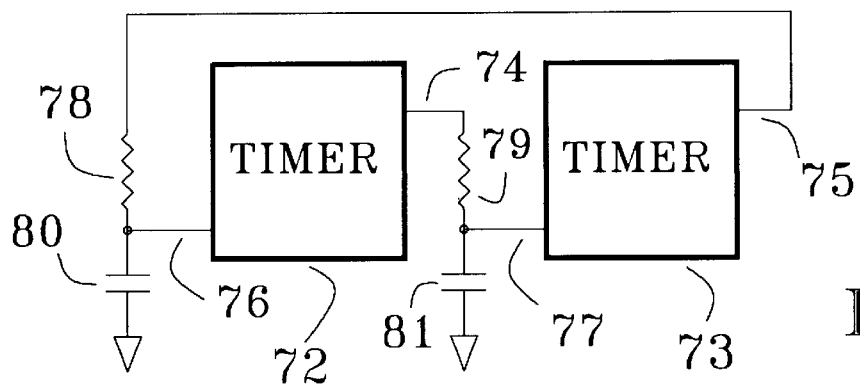
FIG. 5 shows a circuit for producing a chaotic voltage.

A chaotic wave can be generated in a simple manner by cross coupling of two timers. FIG. 5 shows such a hookup, where timers 72 and 73, each labeled "TIMER", have their output pins 74 and 75 connected crosswise to each other's control voltage pins 76 and 77, via resistors 78 and 79. The control voltage pins 76 and 75 have capacitors 80 and 81 to ground. If the timers are hooked up for astable operation with slightly different frequencies, and appropriate values are chosen for the coupling resistors and capacitors, the output of either timer is a chaotic square wave with an oval attractor. Example circuit parameters are: $R_7$=1.22 M$\Omega$, $R_{27}$=1.10 M$\Omega$, $R_{29}$=440 K$\Omega$, $R_{30}$=700 K$\Omega$, $C_8$=0.68 $\mu$f, $C_{28}$=1.0 $\mu$f, $C_{31}$=4.7 $\mu$f, and $C_{32}$=4.7 $\mu$f. For these parameters the output 74 of timer 72 is a chaotic square wave with a power spectrum that has large peaks near 0.40 Hz and 0.62Hz. The chaotic wave is suitable for the excitation of the ½ Hz resonance, and has also been used successfully to control a tremor of non-Parkinson nature.

The voltage generator of FIG. 3 has an oscillator of the RC type, but other types of oscillators can be used. For instance, the generator can be built as a digital device, in which a square wave output is derived from a clock signal by frequency division. Chaotic signals, time variation of frequency, programmed frequency sequences, automatic turn on and shutdown, frequency adjustment, and frequency monitoring may also be accomplished digitally. A computer that runs a simple timing program can be used for the generation of all sorts of square waves that can be made available at a computer port. An economic and compact version of such an arrangement is provided by the Basic Stamp [7], which has an onboard EEPROM that can be programmed for the automatic control of the fluctuating voltage generated, such as to provide desired on/off times, frequency schedules, or chaotic waves. The square waves can be rounded by RC circuits. and further smoothed by integration and filtering.

Figure 6:
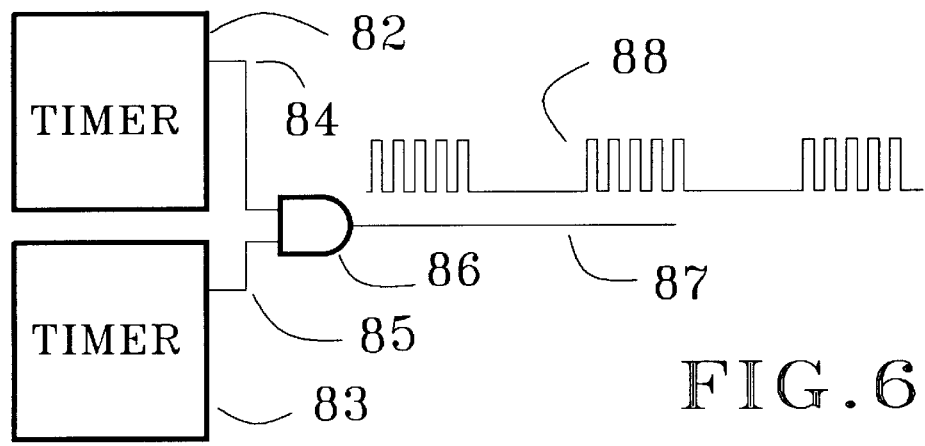
FIG. 6 shows a circuit for generating a complex wave.

For the embodiments shown in FIGS. 1–4, one may use a generator that produces a complex wave, such that the ½ Hz autonomic and the 2.4 Hz cortical sensory resonance are excited together. Such a generator is shown schematically in FIG. 6. Timers 82 and 83 are arranged to produce square waves of frequencies $f_1$ and $f_2$ respectively, where $f_1$ is near 2.4 Hz and $f_2$ is near 0.5 Hz. The outputs 84 and 85 of the timers are connected to the inputs of an AND gate 86. The output 87 of the AND gate produces a square wave of frequency $f_1$, amplitude modulated with a square wave of frequency $f_2$, as indicated by the wave train 88.

For the ½ Hz autonomic resonance, ptosis of the eyelids was used as an indication that the autonomic nervous system is affected. There are two ways in which this indicator may be used. In the first method the subject simply relinquishes control over the eyelids, and makes no effort to correct for any drooping. The more sensitive second method requires the subject to first close the eyes about half way. While holding this eyelid position, the subject rolls the eyes upward, while giving up voluntary control of the eyelids. With the eyeballs rolled up, ptosis will decrease the amount of light admitted into the eyes, and with full ptosis the light is completely shut off. The second method is very sensitive because the pressure excerted on the eyeballs by the partially closed eyelids increases parasympathetic activity. As a result the eyelid position becomes labile, as evidenced by a slight flutter. The labile state is sensitive to small shifts in sympathetic and parasympathetic activity. The method works best when the subject is lying flat on the back and is viewing a blank wall that is dimly to moderately lit.

Immediately after onset of the ½ Hz resonance, the ptosis frequency, defined as the frequency for maximum ptosis, slowly decreases until a steady frequency is reached in 5 to 10 minutes. This is thought to be due to changes in the chemical environment of the resonant neural circuitry, caused by changes in the concentration of neurotransmitters or homones that result from the resonance or from the subsequent change in the autonomic nervous state. The slow shift of ptosis frequency initially is so large that ptosis is lost if the frequency is not adjusted. The ptosis is accompanied by a state of deep relaxation, and often by a slight dull pressure at a spot about 1 cm above the bridge of the nose.

In extensive sleep experiments it has been found that pulse frequencies effective for inducing sleep are somewhat lower than the steady ptosis frequency. Before using a pulsative heating or cooling device for the first time as a sleeping aid, it is recommended that a steady ptosis frequency is first determined by manual scanning and adjusting. Then, starting with this frequency, the subject should adjust the tuning control every few minutes by a small downward frequency step, until sleep sets in. The final tuner setting should be written down in the morning, as it can be used as a fixed setting for the next session.

The experiments on ptosis, relaxation and sleep suggest that pulsative heating or cooling of the skin can diminish sympathetic activity. The method may therefore be applied for the control of panic attacks, when these involve an abnormally high activity of the sympathetic nervous system. In view of the plastic nature of the nervous system, the application may perhaps also serve as a treatment of the disorder.

The method of manipulating the nervous sustem by imparting cooling pulses to the skin may further be applied to the control of disorders, such as tremors and seizures, that involve pathological oscillations of neural circuits. Such oscillations are affected by the chemical milieu, which in turn can be influenced by a sensory resonance. Therefore, by exciting such a resonance through administration of cooling pulses to the skin, the pathological oscillations may be reduced in amplitude or prevented altogether. In view of the plasticity of the nervous system, the method may perhaps also lend itself as a treatment of these disorders.

Figure 10:
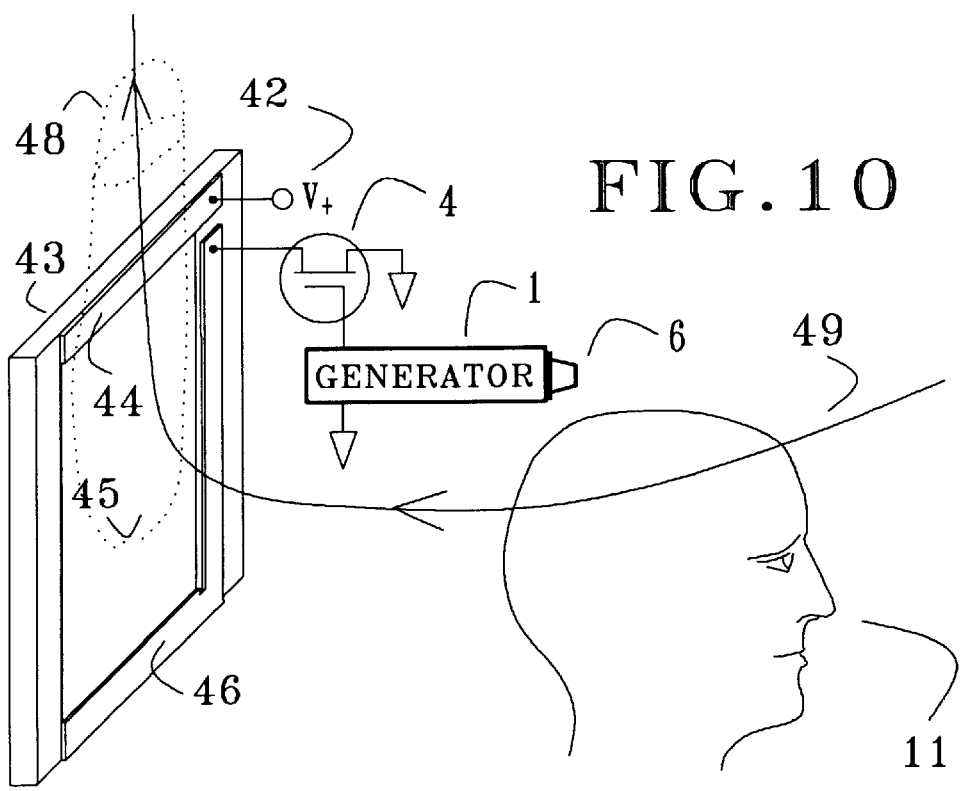
FIG. 10 depicts an embodiment wherein a thin resistive film is used to produce a periodic warm air plume which induces a periodic air sink that causes pulsative air flow past the subject.

In the embodiment of FIG. 1 the thin wires 5 may be seen as a resistor that is in contact with ambient atmospheric air. In FIG. 10 the resistor has the form of a thin resistive film 45 that is present on an insulating substrate 43. The film 45 has distributing strips 44 and 46 which are connected respectively to a voltage $V_+$ indicated by 42, and the drain of a field effect transistor 4. The latter is controlled by voltage pulses from the generator 1, labelled "GENERATOR", which has a tuning control 6. With this arrangement, current is passed through the resistive film 45 in pulsative manner, thereby causing the film temperature to oscillate. As a result, a warm air plume 48 develops periodically adjacent to the film 45. The rising plume draws ambient atmospheric air and thereby causes a pulsative air flow 49 past the face of the nearby subject 11. This airflow imparts cooling pulses to the skin of the subject. The device also induces an acoustic effect similar to the one described for the device of FIG. 1.

The sensory resonance near 2.4 Hz shows up as a considerable increase in the time of silently counting backward from 100 to 60, as fast as possible, with the eyes closed. The counting is done with the "silent voice" which involves motor activation of the larynx appropriate to the numbers to be uttered, but without the passage of air, or movement of mouth muscles. Since counting is a cortical process, the 2.4 Hz resonance may be called a cortical sensory resonance. In addition to affecting the silent counting, the 2.4 Hz resonance is expected to influence some other cortical processes as well. It was found that in the long run the resonance has a sleep inducing effect. Very long exposures have caused dizziness in an environment free of 60 or 50 Hz electromagnetic power fields.

Figure 9:
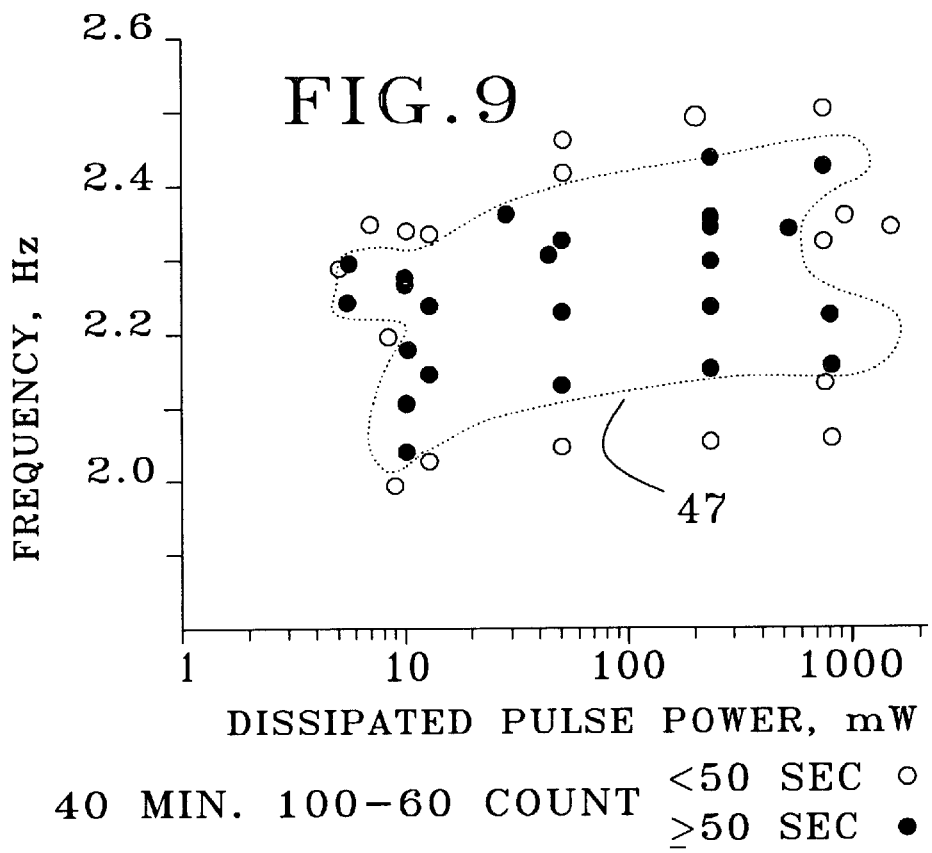
FIG. 9 shows the results of experiments for excitation of the 2.4 Hz sensory resonance with the device of FIG. 1.

The effective intensity window for excitation of the 2.4 Hz resonance with the device of FIG. 1 has been measured in exploratory fashion. The distance between the resistive wire assembly and the subject's head was 50 cm. The experiment comprised 42 runs for a variety of pulse frequencies and pulse powers. At the end of each 40-minute run the time for the silent count from 100 to 60 was measured and recorded. The normal counting time for the subject is about 31 seconds. Results of the experiment are shown in FIG. 9, where dissipated pulse power and pulse frequency of each run is shown by a circle, the open circles denoting counting times less than 50 seconds, and filled circles denoting counting times of at least 50 seconds. Contour 47 separates these two sets of runs. The region inside contour 47 may be called the footprint for the excitation of the 2.4 Hz resonance by the device of FIG. 1. Since data points outside the footprint are sparse, particularly at the low and high power ends, the experiment must be considered merely exploratory. A cross section at fixed pulse frequency gives the effective intensity window of the sensory resonance at this frequency. The footprint is seen to extend roughly from 5 mW to 1 W of dissipated pulse power, and from 2.0 to 2.4 Hz in frequency.

These results need to be compared with exploratory experiments on the 2.4 Hz resonance made through large skin area exposure to blinking heat lamp radiation discussed in U.S. Pat. No. 5,800,481[8]. The latter experiments were done on the same subject about 2 years and 5 months prior to the footprint experiments discussed above. At the time of the earlier experiments we had not yet realized that the larynx stress experienced by the subject in a silent count can influence future counting times, and that counts need to be spaced by 20 minutes or so in order to curb this effect [1]. The data shown in FIG. 11 of ref. [8] give a frequency of about 2.46 Hz and width of roughly 0.13 Hz for the resonance peak measured at a power density of 2.5 mW/cm$^2$, compared to a frequency of about 2.42 Hz (at the largest silent count measured, but not shown in the footprint), and a width of roughly 0.30 Hz for the footprint of FIG. 9. The span of the effective intensity window, defined as the ratio of largest to smallest intensity, is much smaller in FIG. 11 of ref. [8] than in the footprint of FIG. 9. For the former data the span is roughly 3.5, while it is at least 160 for the footprint. The resonance frequencies are in good agreement. However, the discrepancy in the widths, particularly in the window spans, is so large as to suggest that different mechanisms are involved in the two experiments. Such a difference may perhaps be due to the multiple excitation pathways engaged by the device of FIG. 1; as discussed above, these pathways comprise cutaneous thermal receptor afferents and the vestibular nerve. The multiple pathways may also perhaps cause the difference between the slope of the footprint and the much larger shift in resonance frequency with power density, apparent from FIG. 11 of ref. [8].

Figure 12:
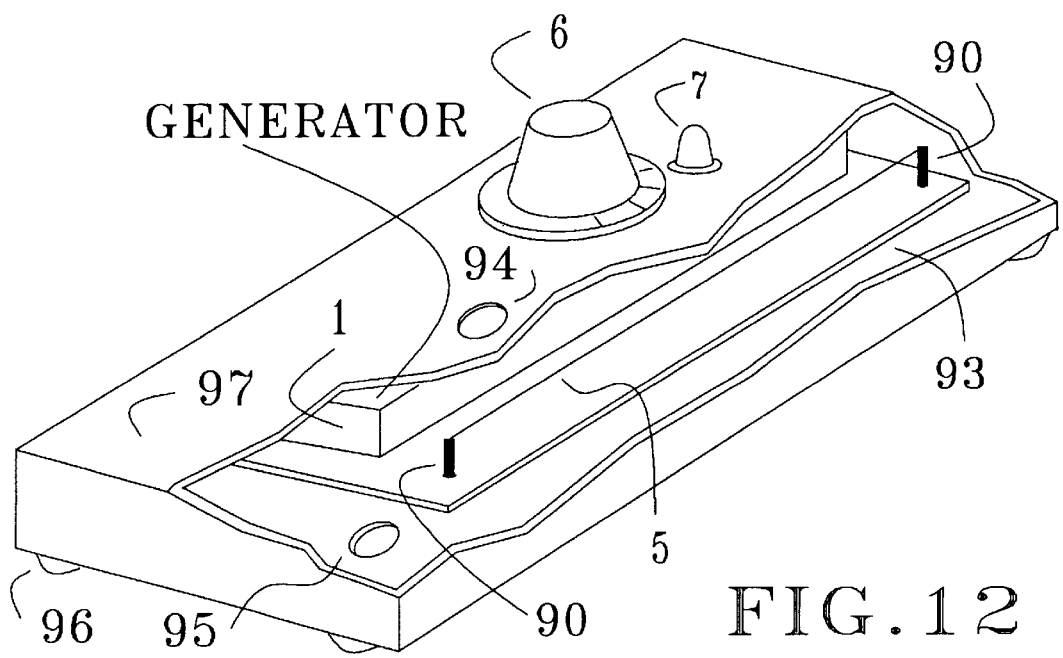
FIG. 12 shows an embodiment wherein a generator and a thin resistive wire are contained in a single small casing.

It can be seen from FIG. 9 that the device of FIG. 1 can excite the 2.4 Hz resonance at a distance of 50 cm with as little as 20 mW pulse power. This makes it possible to drive the resistive wire directly with the generator of FIG. 3, powered by a 3 volt battery. For 2.5 V pulses and a 313 Ω resistive wire the output current is 8 mA and the pulse power is 20 mW. This allows the compact embodiment of FIG. 12, where the generator 1 and the resistive wire 5 are mounted in a single small casing 97, which has ventilation holes 94 and 95 respectively at the top and bottom, and feet 96 such as to give the bottom holes 95 free access to the ambient atmosphere. The resistive wire 5 is mounted by pins 90 directly on the circuit board 93. Shown also are the tuning control 6 and the LED 7. Although for simplicity only a single length of resistive wire 5 is shown in FIG. 12, several wire lengths hooked up in series are needed to bring the resistance to about 313Ω, required by power considerations.

It has been observed that lower temperature pulse amplitudes suffice for the excitation of sensory resonances when the skin area of pulse administration is increased. This "bulk" effect is important for the proper use of the invention, and can be understood as follows. The skin temperature oscillations cause a frequency modulation of the stochastic firing of the cutaneous thermoreceptors. If the afferent fibers of these receptors synapse, either directly or indirectly, upon a summing neuron, then the sequence of current injection spikes into the dendrite of the neuron will be a slightly modulated Poisson stream. For zero modulation a Poisson distribution is expected on theoretical grounds if the number of synapsing afferents is large, since the afferent spike trains add and interlace. This results in a high-frequency sequence of charge injections, in which the features of the individual afferent spike trains are substantially washed out, in much the same way as density nonuniformities of a substance suspended in a fluid are removed by stirring. Whereas the stochastic variations are diminished, the fm variations caused by the skin temperature oscillation add coherently in the hillock potential. As a result, the signal to noise ratio of the fm signal increases with the number of afferents affected [1]. This explains the bulk effect and to some extent the observed sensitivity to very small temperature pulse amplitudes.

The invention is not limited by the embodiments shown in the drawings and described in the specification, which are given by way of example and not of limitation, but only in accordance with the scope of the appended claims.

REFERENCES

[1] H. G. Loos, "Method and Apparatus for Manipulating Nervous Systems", U.S. Pat. No. 5,782,874, Jul. 21, 1998
[2] U.S. Pat. No. 5,935,054, Aug. 10, 1999
[3] E. R. Kandel, J. H. Schwartz, and T. M. Jessel, PRINCIPLES OF NEURAL SCIENCE, 3th Edition, Elsevier, N.Y., 1991
[4] H. Hensel, THERMAL SENSATIONS AND THERMORECEPTORS IN MAN, Charles C. Thomas, Springfield, Ill., 1982
[5] A. Longtin and K. Hinzer, "Encoding with Bursting, Subthreshold Oscillations, and Noise in Mammalian Cold Receptors", Neural Computation 8, 215, (1996)
[6] U.S. Pat. No. 6,017,302, Jan. 25, 2000
[7] Basic Stamp, PARALAX, INC. Rocklin, Calif. 95765
[8] H. G. Loos, "Thermal Excitation of Sensory Resonances", U.S. Pat. No. 5,800,481, Sep. 1, 1998
[9] H. Schlichting, BOUNDARY-LAYER THEORY, McGraw-Hill, New York 1968

I claim:

1. Apparatus for manipulating the nervous system of a subject, comprising:
   generator means for generating voltage pulses;
   cooling means, responsive to the voltage pulses, for convectively imparting pulsative cooling to the skin of the subject; and
   tuning means for tuning the frequency of the voltage pulses.

2. The apparatus of claim 1, wherein the cooling means includes a fan for producing an air jet.

3. The apparatus of claim 2, wherein the air jet has a momentum flux vector, the momentum flux vector varying in pulsative manner in response to the voltage pulses.

4. The apparatus of claim 1, wherein the cooling means includes a resistor in contact with ambient atmospheric air, the resistor having a current and a temperature, the current being responsive to the voltage pulses;

whereby the resistor temperature varies in a pulsating manner, thereby causing a pulsative rising plume of warm air, the plume drawing ambient atmospheric air, said drawing causing a pulsative airflow past the skin of the subject;

whereby convective pulsative cooling is imparted to the skin of the subject.

5. The apparatus of claim 4, further including casing means for containing the generating means and the resistor.

6. The apparatus of claim 1 for exciting in a subject a sensory resonance having a resonance frequency, wherein the voltage pulses have a frequency and wherein the voltage frequency is set to the resonance frequency.

7. Method for manipulating the nervous system of a subject, comprising the steps of:

generating voltage pulses having a frequency;

imparting pulsative cooling to the skin of the subject, by convection the pulsative cooling being responsive to the voltage pulses; and setting the frequency to a value appropriate for excitation of a sensory resonance.

8. The method of claim 7, wherein said convection comprises the steps of:

producing a pulsative warm air plume, the plume drawing air from the ambient atmosphere;

whereby said drawing induces an air flow past the skin of the subject, thereby imparting pulsative cooling to the skin.

9. The method of claim 8, wherein said producing comprises the steps of:

placing a resistor in contact with ambient atmospheric air;

subjecting the resistor to voltage pulses;

whereby the resistor temperature varies in pulsative manner, thereby causing a pulsative warm air plume to rise over the resistor.

10. A method for manipulating the nervous system of a subject, the subject having cutaneous thermoreceptors that produce spike trains which encode skin temperature, the spike trains being transmitted to the brain of the subject by afferent nerves, the method comprising the steps of:

generating voltage pulses having pulse parameters;

convectively imparting cooling pulses to the skin of the subject, the cooling pulses being responsive to the voltage pulses;

whereby the cooling pulses cause a pulsative modulation of said spike trains, the pulsative modulation giving rise to evoked signals in the brain; and selecting the pulse parameters for rendering the evoked signals appropriate for said manipulation.

11. The method of claim 10, for controlling in the subject tremors and seizures, that involve pathological oscillations of neural circuits, the oscillations being affected by the chemical milieu of the neural circuits, the chemical milieu being influenced by a sensory resonance that has a resonance frequency, wherein said pulse parameters include the frequency of the pulses, and wherein said selecting comprises setting the pulse frequency to the resonance frequency.

12. The method of claim 10, wherein said imparting is initiated when the need for said manipulation is perceived.

* * * * *